(12) United States Patent
Donovan

(10) Patent No.: US 7,118,567 B2
(45) Date of Patent: Oct. 10, 2006

(54) METHOD FOR TREATING VULNERABLE PLAQUE

(75) Inventor: Maura G. Donovan, St. Paul, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 149 days.

(21) Appl. No.: 10/835,798

(22) Filed: Apr. 30, 2004

(65) Prior Publication Data
US 2004/0220620 A1   Nov. 4, 2004

Related U.S. Application Data

(60) Provisional application No. 60/467,005, filed on Apr. 30, 2003.

(51) Int. Cl.
*A61B 18/04* (2006.01)

(52) U.S. Cl. .............................. 606/41; 606/32; 606/33

(58) Field of Classification Search ............ 606/27–34, 606/41; 607/96, 98–102
See application file for complete search history.

(56) References Cited

U.S. PATENT DOCUMENTS

| 5,716,379 | A | 2/1998 | Bourgeois et al. | |
|---|---|---|---|---|
| 5,716,392 | A | 2/1998 | Bourgeois et al. | |
| 5,924,997 | A | 7/1999 | Campbell | |
| 6,201,991 | B1 * | 3/2001 | Chekanov | 607/2 |
| 6,245,026 | B1 | 6/2001 | Campbell et al. | |
| 6,475,159 | B1 | 11/2002 | Casscells et al. | |
| 6,475,210 | B1 | 11/2002 | Phelps et al. | |
| 6,786,904 | B1 * | 9/2004 | Doscher et al. | 606/28 |
| 2002/0082515 | A1 * | 6/2002 | Campbell et al. | 600/549 |
| 2002/0099428 | A1 * | 7/2002 | Kaufman | 607/101 |
| 2004/0243022 | A1 * | 12/2004 | Carney et al. | 600/552 |
| 2005/0075704 | A1 * | 4/2005 | Tu et al. | 607/88 |

* cited by examiner

*Primary Examiner*—Roy D. Gibson

(57) ABSTRACT

A method for treating a vulnerable plaque associated with a blood vessel of a patient is disclosed. The method includes positioning an electrical lead adjacent a vulnerable plaque lesion, and then delivering at least one electrical pulse to the lesion.

15 Claims, 4 Drawing Sheets

METHOD FOR TREATING VULNERABLE PLAQUE

RELATED APPLICATION

This application claims priority to U.S. Provisional Application No. 60/467,005, "Method for Treating Vulnerable Plaque" to Maura G. Donovan, filed Apr. 30, 2003, the entirety of which is incorporated by reference.

TECHNICAL FIELD OF THE INVENTION

The present invention relates generally to the field of vascular therapies. More particularly, the invention relates to a method and system for treating a vulnerable plaque associated with a blood vessel of a patient.

BACKGROUND OF THE INVENTION

Heart disease, specifically coronary artery disease, is a major cause of death, disability, and healthcare expense. Until recently, most heart disease was considered primarily the result of a progressive increase of hard plaque in the coronary arteries. This atherosclerotic disease process of hard plaques leads to a critical narrowing (stenosis) of the affected coronary artery and produces anginal syndromes, known commonly as chest pain. The progression of the narrowing reduces blood flow, triggering the formation of a blood clot. The clot may choke off the flow of oxygen rich blood (ischemia) to heart muscles, causing a heart attack. Alternatively, the clot may break off and lodge in another organ vessel such as the brain resulting in a thrombotic stroke.

Within the past decade, evidence has emerged expanding the paradigm of atherosclerosis, coronary artery disease, and heart attacks. While the build up of hard plaque may produce angina and severe ischemia in the coronary arteries, new clinical data now suggests that the rupture of sometimes non-occlusive, vulnerable plaques causes the vast majority of heart attacks. The rate is estimated as high as 60–80 percent. In many instances vulnerable plaques do not impinge on the vessel lumen, rather, much like an abscess they are ingrained under the arterial wall. For this reason, conventional angiography or fluoroscopy techniques are unlikely to detect the vulnerable plaque. Due to the difficulty associated with their detection and because angina is not typically produced, vulnerable plaques may be more dangerous than other plaques that cause pain.

Atherosclerotic plaques vulnerable to rupture are typically small deposits covered by thin fibrous caps (less than 70 microns) covering lipid cores. Within the fibrous cap is a dense infiltrate of smooth muscle cells, macrophages and lymphocytes. Many believe the lipid pool is formed by pathological process involving low-density lipoprotein (LDL), macrophages, and the inflammatory process. The macrophages oxidize the LDL, producing foam cells. The macrophages, foam cells, and smooth muscle cells sit beneath the endothelium and release various toxic substances, such as tumor necrosis factor and tissue factor. These substances damage the arterial wall and surrounding areas and can result in generalized cell necrosis and apoptosis, pro-coagulation, and weakening of the fibrous cap. The inflammation process may weaken the fibrous cap to the extent that sufficient mechanical stress, such as that produced by increased blood pressure, may result in rupture. The lipid core and other contents of the vulnerable plaque (emboli) may then spill into the blood stream thereby initiating a clotting cascade. The cascade produces a blood clot (thrombosis) that potentially results in a heart attack and/or stroke. The process is exacerbated due to the release of collagen and other plaque components (e.g., tissue factor), which enhance clotting upon their release.

Several strategies have been developed for the detection (e.g., diagnosis and localization) of vulnerable plaques. One strategy involves the measurement of temperature within a blood vessel. For example, vulnerable plaque tissue temperature is generally elevated compared to healthy vascular tissue. Measurement of this temperature discrepancy may allow detection of the vulnerable plaque.

Another detection strategy involves labeling vulnerable plaque with a marker. The marker substance may be specific for a component and/or characteristic of the vulnerable plaque. For example, the marker may have an affinity for the vulnerable plaque, more so than for healthy tissue. Detection of the marker may thus allow detection of the vulnerable plaque. Alternatively, the marker may not necessarily have an affinity for the vulnerable plaque, but will simply change properties while associated with the vulnerable plaque. The property change may be detected and thus allow detection of the vulnerable plaque.

Regardless of the strategy used for detection, a formidable problem remains in the treatment of the vulnerable plaque. Without appropriate treatment, the vulnerable plaque may rupture and subsequently release embolic material and cause great risk to the patient, especially when the patient is not in a clinical setting. Drug and other therapies exist that may reduce the size and chance of vulnerable plaque rupture over a relatively long time frame. Percutaneous transluminal coronary angioplasty (PTCA), which is commonly used to treat hard plaques, is contraindicated. In the PTCA procedure, a catheter having an inflatable balloon at its distal end is introduced into the coronary artery, and the balloon is inflated to flatten the hard plaque against the arterial wall. Inflation of a balloon catheter near a vulnerable plaque lesion could rupture the thin fibrous cap that covers the lipid pool, resulting in precisely the clotting cascade that treatment would seek to prevent.

Thickening of the inner wall of a vessel is clearly an unwanted and deleterious side effect when treating hard plaques. However, such thickening could have a positive effect when it serves to strengthen the thin fibrous cap found atop a vulnerable plaque lesion. With the lesion thus stabilized, time is provided for the use of statin drugs or other agents to shrink or remove the lipid pool. These therapies, however, may not be desirable or effective for all patients, including those having vulnerable plaques on the immediate verge of rupture. With such therapies, accidental or unanticipated rupture of these truly vulnerable plaques may occur in a non-clinical setting. Therefore, it would be desirable to provide a treatment strategy that would provide relatively immediate treatment of the vulnerable plaque within a clinical setting. Furthermore, it would be desirable for such a treatment strategy to prevent any embolic material from escaping and causing risk to the patient.

Accordingly, it would be desirable to provide a strategy for treating vulnerable plaque that would overcome the aforementioned and other disadvantages.

SUMMARY OF THE INVENTION

One aspect of the invention provides a method of treating a vulnerable plaque associated with a blood vessel of a patient. The method includes positioning an electrical lead adjacent a vulnerable plaque lesion, and delivering at least one electrical pulse from the electrical lead to the lesion.

Another aspect of the invention provides a method for treating a vulnerable plaque lesion. The method comprises directing an electrical pulse toward a vulnerable plaque lesion for a sufficient time period to thicken a fibrous cap.

An additional aspect of the invention provides a method for treating a vulnerable plaque lesion. This embodiment provides directing an electrical pulse toward a vulnerable plaque lesion for a sufficient time period to stimulate increased capillary growth near the lesion.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENTS

Figure 1:
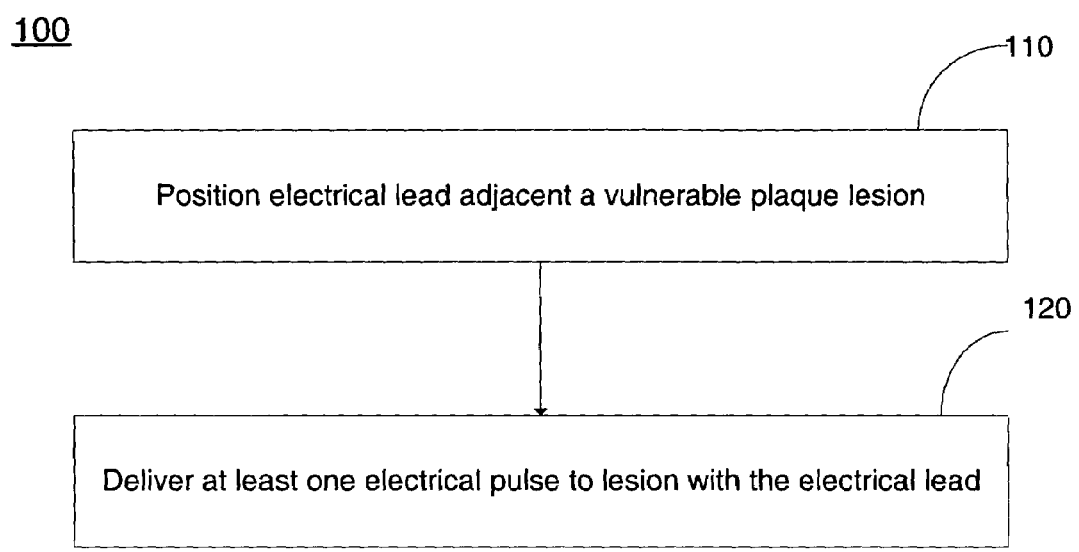
FIG. 1 is a flow chart of a method of treating a vulnerable plaque associated with a blood vessel of a patient, in accordance with one embodiment of the present invention.

FIG. 1 illustrates a flowchart depicting the first embodiment of a method in accordance with the instant invention. Method 100 begins at block 110 where an electrical lead is positioned adjacent a vulnerable plaque lesion.

Figure 2:
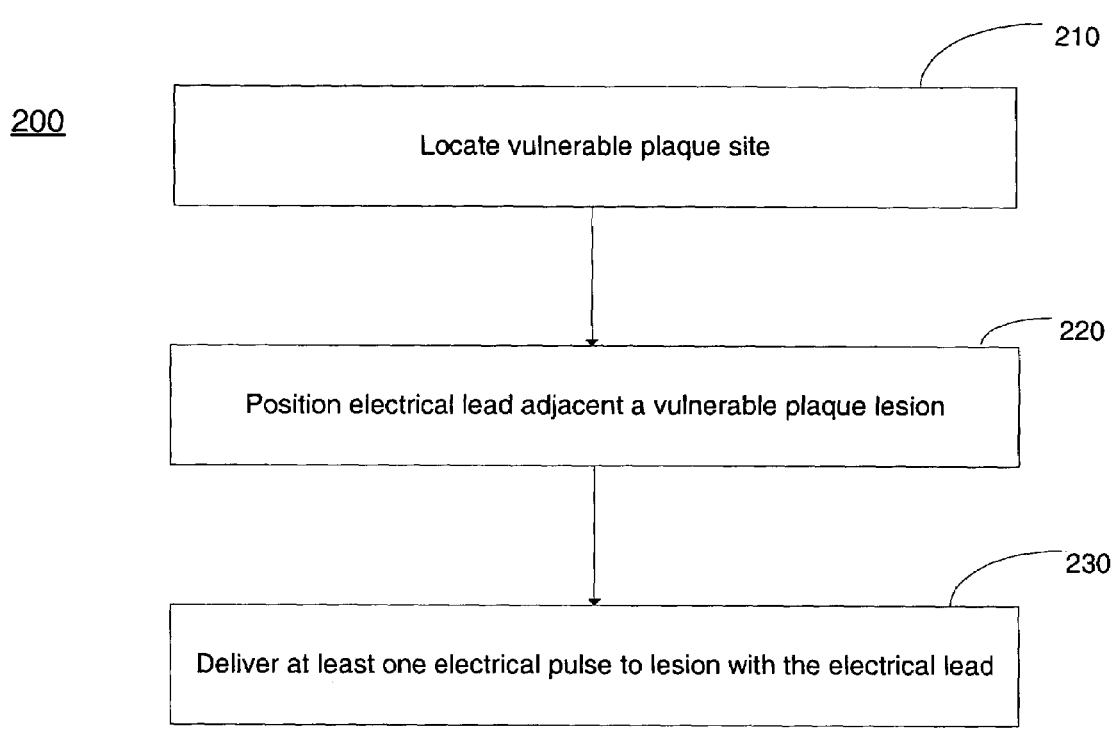
FIG. 2 is a flow chart of a method of treating a vulnerable plaque lesion, in accordance with another embodiment of the present invention.

In the following description, vulnerable plaque treatment is described in the context of a catheterization detection and treatment procedure for a patient. The vulnerable plaque may be treated in a clinical setting thereby allowing for controlled treatment in an environment in which immediate care is given. Treating the vulnerable plaque in a manner according to the present invention may prevent the accidental or unanticipated release of emboli in a non-clinical setting. As such, complications stemming from vulnerable plaque rupture, such as heart attack and stroke, may be avoided. It should be noted that the terms "detect" and derivatives thereof, when used in regard to vulnerable plaque, refer to the diagnosis and localization of the lesion Prior to positioning the electrical lead, it may be desirable to predetermine one or more treatment sites including vulnerable plaque. This aspect of the invention is shown in FIG. 2, as block 210. The treatment site(s) may be located during a vulnerable plaque diagnostic procedure. Numerous such detection procedures are known in the art and may be adapted for use with the present invention. The strategies include, but are not limited to, temperature detection strategies, labeling strategies, imaging strategies, general strategies for discriminating the vulnerable plaque from surround healthy vascular tissue, and the like.

The temperature detection strategies may include a comparison of the temperature of various portions of a blood vessel. The temperature of the vulnerable plaque is typically one or more degrees Celsius higher than healthy vascular tissue because of increased metabolic activity (i.e., inflammation). For example, a relatively normal blood vessel temperature may be about 37° C. whereas the vulnerable plaque may have a localized temperature as high as 40° C. As such, the temperature-sensing device may be used to detect vulnerable plaque(s). Numerous devices for sensing temperature are known in the art. By way of example, the temperature-sensing device may be a thermography catheter analogous to that described in U.S. Pat. No. 6,245,026 to Campbell et al. and U.S. Pat. No. 6,475,159 to Casscells et al. As another example, a guidewire including thermal sensors and any number of other devices known in the art may be used for sensing vessel temperature and detecting the vulnerable plaque.

Other detection strategies may utilize any number of properties specific to a vulnerable plaque for detection. For example, vulnerable plaques generally include a localized concentration of specific lipids, proteins, and factors. Measurement of these components may facilitate detection. The detection may be achieved and/or enhanced by labeling. For example, the vulnerable plaque may be labeled with an antibody marker specific for a plaque component wherein the antibody may include a radiolabel. The radiolabel may then be detected with an appropriate detection device known in the art.

The vulnerable plaque may be detected endovascularly as with, for example, a catheter based platform. By way of example, the endovascular device may be a light treatment catheter analogous to that described in U.S. Pat. No. 6,475,210 to Phelps et al. Alternatively, the vulnerable plaque may be detected from external the blood vessel. For example, a device for detecting the vulnerable plaque may be positioned through an incision in the patient. The device may then detect the vulnerable plaque without the need for catheterization. During such a procedure, detection may be achieved during open surgery or in a minimally invasive manner. As another example, the vulnerable plaque may be detected external to the patient, such as with an imaging device (e.g., devices utilizing magnetic resonance, ultrasound, infra-red, fluorescence, visible light, radio waves, x-ray, etc.). Those skilled in the art will recognize that the strategy for detecting the vulnerable plaque may vary from the described methods. Numerous methods and devices for the detection of vulnerable plaque may be adapted for use with the present invention.

The vulnerable plaque diagnostic procedure may be performed in a previous procedure distinct from treatment or, alternatively, as a common medical procedure. Furthermore, to practice the instant invention, the diagnostic procedure need not detect the precise location of the vulnerable plaque(s). The treatment procedure of the present invention may be employed in vascular region(s) merely suspected of including vulnerable plaque (i.e., a prophylactic-type treatment). For example, a patient determined to have an elevated risk of vulnerable plaque may undergo a treatment strategy in accordance with the present invention, and especially the embodiment depicted in FIG. 1, at various region(s) generally known to include such plaques.

After the lesion has been located, positioning the electrical lead next requires accessing a target area. Numerous methods may used to access the target area. In some embodiments of the invention, a catheter-based system will be used to position the electrical lead. Catheter-based systems are well known in the art, and generally comprise a catheter that is guided to the target area using a guidewire. The catheter is slidably attached to the guidewire via a lumen in the body of the catheter, such that the catheter surrounds the guidewire lumen, and slides along the guidewire. Such systems are generally monitored for accurate placement with imaging technologies, such as fluoroscopy, and may comprise the use of radio-opaque dyes. Catheter-based systems may include other devices as well, and may include the detection means as described above.

Other delivery systems may also be used. In another embodiment of the instant invention, the lead may be positioned through a thoracotomy. In a thoracotomy, an opening is created in the thoracic area of a body. Use of a thoracotomy for positioning the lead may prove advantageous for positioning the lead in certain positions within the thoracic region. In a thoracotomy placement of the electrical lead, a thoracotomy is made to provide access to the target area, and the electrical lead is placed in the desired position after passing through the thoracotomy.

Another embodiment of the instant invention includes using a laparoscopic approach to positioning the electrical lead. Laparoscopy is a surgical technique that uses a series of smaller incisions, large enough to allow insertion of a light, and appropriate surgical tools. Although laparoscopy is less invasive than a thoracotomy, it may not always be preferred to use a laparoscopic approach. In a laparoscopic placement of the electrical lead, appropriate incisions are made to provide access to the target area, and the electrical lead is threaded through the incisions and placed in the desired position.

Yet another embodiment of the instant invention comprises the use of open surgical techniques to position the electrical lead. Although this is perhaps the most invasive technique, it may be preferred for locating the electrical lead in certain positions.

The lead may be positioned at any appropriate location to deliver the at least one electrical pulse. One embodiment comprises locating the lead directly within a blood vessel. Such an embodiment is likely to entail use of a catheter-based system. The electrical lead may be placed directly in the blood vessel that comprises the vulnerable plaque lesion, such that no vessel wall is in the path of the electrical pulses. In another embodiment of the invention, the electrical lead may be placed in a blood vessel that is not the same blood vessel that comprises the vulnerable plaque. In such an embodiment, at least two vessel walls will be in the path of the electrical pulse—the vessel wall containing the electrical lead, and the vessel wall comprising the vulnerable plaque lesion.

In another embodiment, the electrical lead is positioned epicardially. In an epicardial placement, the electrical lead is placed in an epicardial position, adjacent the heart. The placement may be performed endovascularly, or may be positioned with a thoracotomy, laparoscopic techniques, or open surgical techniques. Placement of a different electrical device is disclosed in U.S. Pat. No. 5,716,379, issued Feb. 10, 1998 to Bourgeois et. al., which is assigned to the same assignee as this application. FIG. 1 of the '379 patent illustrates a cardiac assist device having muscle augmentation prior to defibrillation, in an epicardial position.

In yet another embodiment of the instant invention, the electrical lead may be placed directly into a chamber of a heart, and in some embodiments, an atrium of the heart. The location of certain vulnerable plaque lesions may require that the electrical lead be placed directly into the heart. In such a case, positioning of the electrical lead may still be obtained using the above surgical methods. Positioning the lead in the heart may indicate further treatment options, especially if the electrical lead is placed into a ventricle. Placement into an atrium may require fewer additional treatment options than placement of the lead directly into a ventricle. These treatment options, and the factors for their indication, are known to those of ordinary skill in the art.

After the electrical lead has been positioned adjacent a vulnerable plaque lesion, method 100 continues at block 120. At block 120, the electrical lead is used to deliver at least one electrical pulse to the vulnerable plaque lesion. In one embodiment, the electrical lead delivers the pulse after voltage is applied to the electrical lead. Other embodiments of the invention may deliver the electrical pulse by retracting a protective sheath from the lead. The lead may be any appropriate electrical device, including electrodes. One lead that may be appropriate for use is disclosed in U.S. Pat. No. 5,716,392, issued Feb. 10, 1998 to Bourgeois et al. and assigned to the same assignee as this application. The '392 patent discloses a minimally invasive medical electrical lead, as illustrated in FIG. 5 of the '392 patent.

The electrical pulse may be a high frequency, low voltage pulse. The pulse may be delivered with a pulse generator for biomedical applications. Pulse generators for delivering a pulse of electricity to a body part are known in the art. One example of such a pulse generator is described in the '379 patent, although any appropriate pulse generator may be used in practicing this invention. The frequency and voltage are selected from ranges appropriate for cardiac treatment.

The electrical pulse may be applied for a specific time period. This period may be calculated to increase the thickness of the thin fibrous cap that covers vulnerable plaque lesions.

Subthreshold stimulation promotes production of angiogenic growth factors with an electric field of 0.1 V/cm (Volts/centimeters) through 1V/cm with a frequency from 10–100 Hertz (Hz). In a currently preferred embodiment, a field of 0.1 V/cm, at 50 Hz is applied for 0.1–3 milliseconds.

Alternatively, a field with a current density of 60 microamperes/$mm^2$ lasting 10 milliseconds at a frequency of 10 Hz increases production of thrombolytic peptides by the vascular endothelial cells. The amplitude of this current may range from 0.1 V to 25 V (volts). When such a field is applied, the device applying the stimulation would include heart pacemaking capabilities to pace the heart to facilitate synchronization of the electrical current generation with the refractory period of the heart. This field also promotes local accumulation of charged proteins and growth factors, moving the endothelial cells to modulate cell proliferation and differentiation, stimulating extra-cellular matrix production. These growth factors include VEGF, FGF, TGFBeta and BMP-2. Accumulation of the charged proteins and growth factors thickens the fibrous cap.

Application of the high frequency, low voltage electrical pulse near the vulnerable plaque lesion may also have an anti-proliferative effect. Such an effect is characterized by reducing growth of a vulnerable plaque lesion. Although anti-proliferative effects do not eliminate the vulnerable plaque lesion, any adverse effects of the vulnerable plaque lesion may be reduced by reducing any growth of the lesion.

Application of the high frequency, low voltage electrical pulse near the vulnerable plaque lesion may also increase the thickness of the thin fibrous cap or covering that covers a lipid pool of the vulnerable plaque lesion. Such an effect may reduce the chances of a rupture of the thin fibrous cap, and may minimize the potentially adverse effects of the rupture.

FIG. 2 is a flow chart of a method of treating a vulnerable plaque associated with a blood vessel of a patient, in accordance with one embodiment of the present invention. A vulnerable plaque is distinguishable from other types of plaque, including hard plaques, by the presence of a relatively thin fibrous cap. The vulnerable plaque fibrous cap retains a pool of lipids and other contents, which may be released into the blood vessel upon rupture of the cap. The released contents and any resulting blood clots constitute emboli that can lodge in a blood vessel thereby posing a risk to the patient. Vulnerable plaques, unlike hard plaques, are generally non-occlusive and, as such, may not produce angina. The following description pertains to treatment of these vulnerable plaques.

At block 210, a vulnerable plaque site is located. Several techniques for locating and detecting such lesions exist, and may include the use of imaging techniques. For example, X-rays may be used. In other embodiments, more advanced imaging technologies may be applied, including tomographic scanning or magnetic resonance imaging.

Other methods of identifying vulnerable plaques have been proposed. These include sensing the temperature differential between healthy vascular tissue and the inflamed tissue of a vulnerable plaque. Devices that identify vulnerable plaques by the higher temperature of the inflamed tissue have been described in, for example, U.S. Pat. No. 5,924,997 to Campbell and U.S. Pat. No. 6,475,159 to Casscells et al.

Detection techniques are described in detail above, and that discussion is equally applicable to an understanding of the embodiment of the invention disclosed in FIG. 2.

At block 220, an electrical lead is positioned adjacent the vulnerable plaque lesion. After the lesion has been located, positioning the electrical lead next requires accessing a target area. Numerous methods may used to access the target area. In some embodiments of the invention, a catheter-based system will be used to position the electrical lead. Catheter-based systems are well-known in the art, and generally comprise a catheter which is guided to the site using a guidewire. The catheter is slidably attached to the guidewire via a lumen in the body of the catheter, such that the catheter surrounds the guidewire lumen, and slides along the guidewire. Such systems are generally monitored for accurate placement with imaging technologies, such as fluoroscopy, and may comprise the use of radio-opaque dyes. Catheter-based systems may include other devices as well, and may include the detection means as described above.

Other delivery systems may also be used. In another embodiment of the instant invention, the lead may be positioned through a thoracotomy. In a thoracotomy, an opening is created in the thoracic area of a body. Use of a thoracotomy for positioning the lead may prove advantageous for positioning the lead in certain positions within the thoracic region. In a thoracotomy placement of the electrical lead, a thoracotomy is made to provide access to the target area, and the electrical lead is placed in the desired position after passing through the thoracotomy.

Another embodiment of the instant invention includes using a laparoscopic approach to positioning the electrical lead. Laparoscopy is a surgical technique that uses a series of smaller incisions, large enough to allow insertion of a light, and appropriate surgical tools. Although laparoscopy is less invasive than a thoracotomy, it may not always be preferred to use a laparoscopic approach. In a laparoscopic placement of the electrical lead, appropriate incisions are made to provide access to the target area, and the electrical lead is threaded through the incisions and placed in the desired position.

Yet another embodiment of the instant invention comprises the use of open surgical techniques to position the electrical lead. Although this is perhaps the most invasive technique, it may be preferred for locating the electrical lead in certain positions.

The lead may be positioned at any appropriate location to deliver the at least one electrical pulse. One embodiment comprises locating the lead directly within a blood vessel. Such an embodiment is likely to entail use of a catheter-based system. The electrical lead may be placed directly in the blood vessel that comprises the vulnerable plaque lesion, such that no vessel wall is in the path of the electrical pulses. In another embodiment of the invention, the electrical lead may be placed in a blood vessel that is not the same blood vessel that comprises the vulnerable plaque. In such an embodiment, at least two vessel walls will be in the path of the electrical pulse—the vessel wall containing the electrical lead, and the vessel wall comprising the vulnerable plaque lesion.

In another embodiment, the electrical lead is positioned epicardially. In an epicardial placement, the electrical lead is placed in an epicardial position, adjacent the heart. The placement may be in a blood vessel, or may be positioned with a thoracotomy, laparoscopic techniques, or open surgical techniques. Placement of a different electrical device is disclosed in U.S. Pat. No. 5,716,379, issued Feb. 10, 1998 to Bourgeois et. al, which is assigned to the same assignee as this application. FIG. 1 of the '379 patent illustrates a cardiac assist device having muscle augmentation prior to defibrillation, in an epicardial position.

In yet another embodiment of the instant invention, the electrical lead may be placed directly into a chamber of a heart, and in some embodiments, an atrium of the heart. The location of certain vulnerable plaque lesions may require that the electrical lead be placed directly into the heart. In such a case, positioning of the electrical lead may still be obtained using the above surgical methods. Positioning the lead in the heart may indicate further treatment options, especially if the electrical lead is placed into a ventricle. Placement into an atrium may require fewer additional treatment options than placement of the lead directly into a ventricle. These treatment options, and the factors for their indication, are known to those of ordinary skill in the art.

After the electrical lead has been positioned adjacent a vulnerable plaque lesion, method 200 continues at block 230. At block 230, the electrical lead is used to deliver at least one electrical pulse to the vulnerable plaque lesion. In one embodiment, the electrical lead delivers the pulse after voltage is applied to the electrical lead. Other embodiments of the invention may deliver the electrical pulse by retracting a protective sheath from the lead. The lead may be any appropriate electrical device, including electrodes. One lead that may be appropriate for use is disclosed in U.S. Pat. No. 5,716,392, issued Feb. 10, 1998 to Bourgeois et al. and assigned to the same assignee as this application. The '392 patent discloses a minimally invasive medical electrical lead, as illustrated in FIG. 5 of the '392 patent.

The electrical pulse may be a high frequency, low voltage pulse. The pulse may be delivered with a pulse generator for biomedical applications. Pulse generators for delivering a pulse of electricity to a body part are known in the art. One example of such a pulse generator is described in the '379 patent, although any appropriate pulse generator may be used in practicing this invention. The frequency and voltage are selected based on ranges appropriate for cardiac treatment.

Subthreshold stimulation promotes production of angiogenic growth factors with an electric field of 0.1 V/cm (Volts/centimeters) through 1V/cm with a frequency from 10–100 Hertz (Hz). In a currently preferred embodiment, a field of 0.1 V/cm, at 50 Hz is applied for 0.1–3 milliseconds.

Alternatively, a field with a current density of 60 microamperes/mm$^2$ with a 10 millisecond duration and 10 Hz frequency increases thrombolytic peptides by the vascular endothelial cells. The amplitude of this current may range from 0.1 V to 25 V (volts). When such a field is applied, the device applying the stimulation would include heart pacemaking capabilities to pace the heart to facilitate synchronization of the electrical current generation with the refractory period of the heart. This field also promotes local accumulation of charged proteins and growth factors, moving the endothelial cells to modulate cell proliferation and differentiation, stimulating extra-cellular matrix production. These growth factors include VEGF, FGF, TGFBeta and BMP-2. Accumulation of the charged proteins and growth factors thickens the fibrous cap.

Figure 3A:
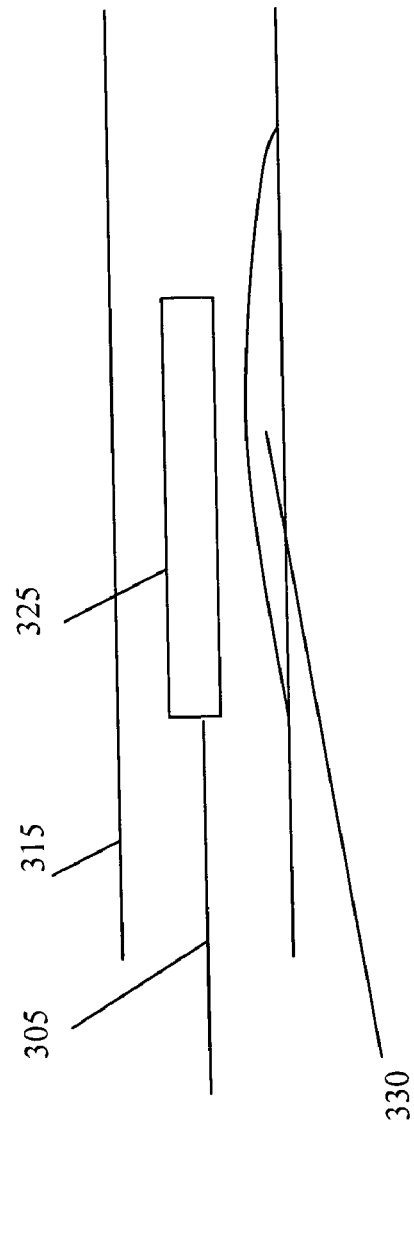
FIGS. 3A, 3B, and 3C are illustrations of one embodiment of a device for treating a vulnerable plaque lesion in accordance with one embodiment of the invention.
Figure 3B:
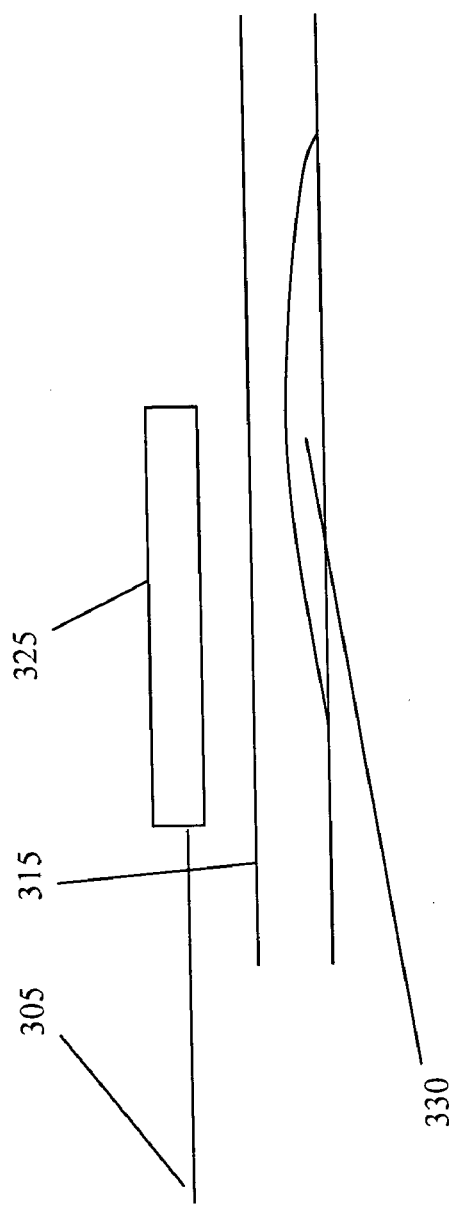
Figure 3C:
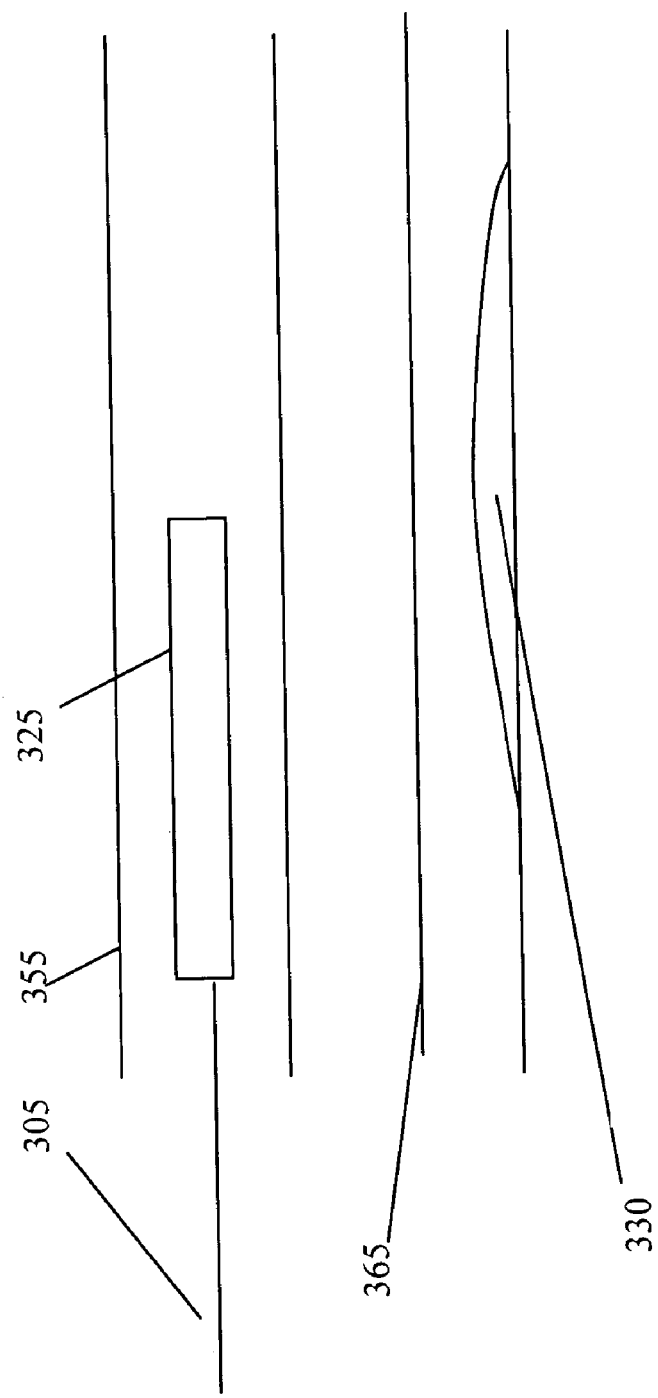

FIGS. 3A, 3B and 3C illustrate an electrical lead positioned adjacent a vulnerable plaque lesion in accordance with embodiments of the invention. In the embodiment illustrated in FIG. 3A, lead 325 is positioned inside vessel 315 adjacent a vulnerable plaque lesion 330 in vessel 315. Lead 325 is connected to an electricity source (not shown) with wire 305. FIG. 3B illustrates lead 325 positioned in the extravascular space, exterior to vessel 315, but still adjacent to vulnerable plaque lesion 330. FIG. 3C illustrates lead 325 positioned within a vessel 355 adjacent vessel 365 containing vulnerable plaque lesion 330. Vessel 355 may be a different region of vessel 365, or vessel 355 may be an entirely different vessel than vessel 355.

Those skilled in the art will recognize that although the present invention is described primarily in the context of treating a vulnerable plaque while using specific treatment devices, the inventor contemplates a broader method of application. Any number of treatment devices capable of performing the prescribed function(s) may be compatible with the present invention. Furthermore, the treatment of the vulnerable plaque is not limited to the described methodology. Numerous modifications, substitutions, and variations may be made to the method and system while providing effective vulnerable plaque treatment consistent with the present invention.

While the embodiments of the invention disclosed herein are presently considered preferred, various changes and modifications may be made without departing from the spirit and scope of the invention. The system, device(s), and method of utilizing the same are not limited to any particular design or sequence. Specifically, the system and device components, procedure step order, and method of achieving the same may vary without limiting the utility of the invention. Upon reading the specification and reviewing the drawings hereof, it will become immediately obvious to those skilled in the art that myriad other embodiments of the present invention are possible, and that such embodiments are contemplated and fall within the scope of the presently claimed invention. The scope of the invention is indicated in the appended claims, and all changes that come within the meaning and range of equivalents are intended to be embraced therein.

What is claimed is:

1. A method of treating vulnerable plaque, the method comprising:
    positioning an electrical lead adjacent a vulnerable plaque lesion in a vessel; and
    delivering at least one electrical pulse from the electrical lead to the vulnerable plaque lesion, wherein the pulse is delivered for a time period sufficient to thicken a fibrous cap of the lesion.

2. The method of claim 1 wherein positioning the electrical lead adjacent the vulnerable plaque lesion comprises delivering the electrical lead through a vessel via a catheter.

3. The method of claim 2 wherein the vessel through which the electrical lead is delivered is adjacent the vessel having the lesion.

4. The method of claim 2 wherein the catheter is inserted in the vessel having the lesion.

5. The method of claim 1 wherein positioning the electrical lead adjacent the vulnerable plaque lesion comprises delivering the electrical lead epicardially.

6. The method of claim 1 wherein the at least one electrical pulse is a high frequency, low voltage pulse.

7. The method of claim 6 wherein the at least one electrical pulse has a frequency of 50 Hertz and a voltage of 0.1 Volts/centimeter.

8. The method of claim 6 wherein the at least one electrical pulse has a frequency of 10 Hertz, a voltage of 0.1 Volts/centimeter to 25 Volts/centimeter, and a current density of 60 microamperes/millimeter$^2$.

9. The method of claim 1 wherein positioning the electrical lead adjacent the vulnerable plaque comprises delivering through a thoracotomy.

10. The method of claim 1 wherein positioning the electrical lead adjacent the vulnerable plaque comprises delivering through a laparoscope 11. The method of claim 1 wherein positioning the electrical lead adjacent the vulnerable plaque comprises placing the electrical lead within a chamber of a heart.

12. The method of claim 11 wherein the chamber of a heart comprises an atrium.

13. The method of claim 1 wherein the pulse is delivered for a time period sufficient to increase angiogenic growth.

14. A method of treating vulnerable plaque comprising:
    directing at least one electrical pulse toward a vulnerable plaque lesion for a sufficient time period to thicken a fibrous cap of the vulnerable plaque lesion.

15. A method of treating vulnerable plaque comprising:
    directing at least one electrical pulse toward a vulnerable plaque lesion for a sufficient time period to increase capillary growth near the vulnerable plaque.

* * * * *